United States Patent
Yu et al.

(10) Patent No.: US 10,323,247 B2
(45) Date of Patent: Jun. 18, 2019

(54) METHODS FOR IMPROVING EXPRESSION LEVELS OF FOREIGN PROTEINS BY MEANS OF PHOSPHOLIPASE FUSION EXPRESSION

(71) Applicants: Xiaowei Yu, Wuxi (CN); Yan Xu, Wuxi (CN)

(72) Inventors: Xiaowei Yu, Wuxi (CN); Yan Xu, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 15/995,134

(22) Filed: Jun. 1, 2018

(65) Prior Publication Data
US 2018/0265876 A1     Sep. 20, 2018

Related U.S. Application Data

(63) Continuation of application No. PCT/CN2016/071043, filed on Jan. 15, 2016.

(51) Int. Cl.
| | |
|---|---|
| *C12N 9/20* | (2006.01) |
| *C12N 15/00* | (2006.01) |
| *C12N 1/20* | (2006.01) |
| *C12P 21/06* | (2006.01) |
| *C12P 21/04* | (2006.01) |
| *C12N 1/14* | (2006.01) |
| *C07H 21/04* | (2006.01) |

(Continued)

(52) U.S. Cl.
CPC .............. *C12N 15/62* (2013.01); *C07K 14/38* (2013.01); *C12N 9/20* (2013.01); *C12N 9/50* (2013.01); *C12N 15/81* (2013.01); *C12Y 301/01004* (2013.01); *C07K 2319/61* (2013.01)

(58) Field of Classification Search
None
See application file for complete search history.

(56) References Cited

FOREIGN PATENT DOCUMENTS

| CN | 102654504 A | 9/2012 |
|---|---|---|
| WO | 2009023270 A2 | 2/2009 |

OTHER PUBLICATIONS

Li. Machine translation of CN 102654504. retrieved from https://worldwide.espacenet.com/?locale=EN_ep on Oct. 15, 2018.*

(Continued)

*Primary Examiner* — Yong D Pak
(74) *Attorney, Agent, or Firm* — Lili Chen

(57) ABSTRACT

The invention discloses a method for improving the extracellular expression level of a foreign protein by means of phospholipase fusion expression. Four proteins, $PLA_2$, MBP, CBD and SUMO, are used as a fusion tag to construct a fusion gene. Compared with an original protein MOH without any fusion tag, the extracellular expression level and enzymatic activity of all the four fusion proteins are increased to some degree. Among them, the fusion protein using $PLA_2$ as the fusion tag has the highest expression level, which is 7.4 times higher than that of the original protein. Compared with other fusion tags, $PLA_2$ has a low molecular weight and the fusion protein having PLA2 as the fusion tag has the highest expression level (up to $12 \text{ g} \cdot \text{L}^{-1}$ in a 7 L fermentation tank for high-density fermentation). It is shown that the secretory expression of a foreign protein can be effectively increased by using $PLA_2$ as a fusion tag.

10 Claims, 7 Drawing Sheets
Specification includes a Sequence Listing.

Structure of the Fusion Gene

(51) Int. Cl.
    *C07K 1/00*           (2006.01)
    *C12N 15/62*         (2006.01)
    *C07K 14/38*         (2006.01)
    *C12N 15/81*         (2006.01)
    *C12N 9/50*           (2006.01)

(56) References Cited

OTHER PUBLICATIONS

Jiang. High-level expression of prolyl endopeptidase in Pichia pastoris usingPLA2as a fusion partner. Journal of Molecular Catalysis B: Enzymatic 125 (2016) 81-87.*

Kang, Chao et al. "Cloning and expression of a novel prolyl endopeptidase from Aspergillus Oryzea and its application in beer stabilization", Journal of Insdustrial Microbiology and Biotechnology, vol. 42, No. 2, Dec. 30, 2014.

* cited by examiner

Structure of the Fusion Gene

METHODS FOR IMPROVING EXPRESSION LEVELS OF FOREIGN PROTEINS BY MEANS OF PHOSPHOLIPASE FUSION EXPRESSION

CROSS-REFERENCES AND RELATED APPLICATIONS

This application is a continuation of the international application PCT/CN2016/071043, with an international filing date of Jan. 15, 2016, the content of which is herein incorporated by reference in its entirety.

BACKGROUND OF THE INVENTION

Field of the Invention

The disclosure relates to the field of bioengineering, and more particularly relates to a method for improving expression levels of foreign proteins by means of phospholipase fusion expression.

Description of the Related Art

Prolyl endopeptidase (PEP for short) [EC 3.4.21.26] does not belong to a typical serine protease family, but is a special serine protease, which is known as prolyl endopeptidase family together with *escherichia coli* protease II (protease II). The molecular weight of most prolyl endopeptidase is about 75 KDa, the optimum temperature is about 45° C., and the optimum pH is about 4.5. Prolyl endopeptidase is a site-specific protease that can specifically hydrolyze a proline carboxy-terminal peptide bond in a molecular polypeptide (the rate of hydrolysis of small peptides is much higher than that of macromolecular peptides). Prolyl endopeptidase can also act on alanine residues but with much less hydrolysis efficiency.

Prolyl endopeptidase has important applications in biomedical therapy, which makes it a hotspot of international biomedical research. PEP can degrade many polypeptide neurotransmitters and hormones, and the aberrant activity of PEP can cause learning and spatial memory disorder. PEP can be applied to Alzheimer's disease and regulation of glucose metabolism and pancreatic functions. Therefore, further study of the physiological functions of the enzyme and development of inhibitors of the enzyme to treat memory disorders can bring great social and economic benefits.

Almost all protein hydrolysates have different levels of bitterness, mainly due to the existence of hydrophobic amino acids (such as proline), and the degree of bitterness is positively correlated with the content of hydrophobic amino acids. Edens et al. found that the prolyl endopeptidase obtained from *Aspergillus niger* through extracellular extraction and purification can effectively remove the bitterness of a bitter casein hydrolysate.

Celiac disease is the T-cell-predominant intolerance to bran of plants including wheat and the like. Gluten-mediated T-cell immune epitopes are abundant in proline and are therefore highly resistant to protein degradation in the gastrointestinal tract. Common prolyl endopeptidase oral preparations have many limitations, for example, low stability in a low-pH environment, high sensitivity to pepsin, and inability to completely digest all gluten in normal diets of each meal. Stepniak et al. obtained a novel prolyl endopeptidase (AN-PEP) from *Aspergillus niger*, and the novel prolyl endopeptidase can effectively reduce glutenin content in an in vitro simulated gastrointestinal environment and overcome many defects mentioned above.

Lopez et al. found that the addition of a very small amount of specific acidic prolyl endopeptidase during bottled beer fermentation can effectively prevent the problem of cold turbidity in the beer production process while the foam stability of beer is not affected. In addition, compared with the silica gel and PVPP method, the PEPase treatment method also has an advantage in terms of processing: no need to treat raw materials. The proteins that cause turbidity and precipitation during beer storage are mainly special proline-rich peptides. Proline endoprotease can be used for decomposing such turbidity-causing proteins so as to improve the non-biological stability of the beer. This can replace the current treatment methods used for improving beer colloid stability.

In addition, PEP can be used as an instrumental enzyme in molecular biology applications such as protein sequence determination, peptide mapping analysis, digestion of specific loci, peptide chain modification and processing, and the like.

Since the prolyl endopeptidase has many important functions, some researchers have already exogenously expressed the prolyl endopeptidase. For example, in 1980, Japanese researchers identified Flavobacterium meningosepticum capable of producing the prolyl endopeptidase, and enzyme activity reached 34.5 $U \cdot g^{-1}$ after purification (wet cells). Subsequently, the research team introduced the PEP gene into *Escherichia coli* for exogenous expression 558 $U \cdot g^{-1}$ (wet cells). In 1993, the prolyl endopeptidase derived from Aeromonas hydrophila was cloned and expressed in *Escherichia coli* JM83, and enzyme activity reached 320 $U \cdot g^{-1}$. However, the exogenous expression activity of the prolyl endopeptidase is still not very high. Therefore, there is a need to develop an effective strategy to improve the expression level of PEP in foreign hosts.

DETAILED DESCRIPTION

In order to overcome the above problems, the invention provides a method for improving the expression level of a foreign protein by means of phospholipase fusion expression, a genetically engineered yeast obtained by the method and applications thereof.

The first objective of the invention is to provide a fusion gene, wherein the fusion gene is obtained by sequentially ligating a gene fragment encoding a fusion tag, a gene fragment encoding a linker peptide and a gene fragment encoding a foreign protein.

In one embodiment of the invention, the fusion tag is any one of phospholipase A2 (PLA2), cellulose binding domain (CBD), small ubiquitin-related modifier (SUMO) and maltose binding protein (MBP).

In one embodiment of the invention, the fusion tag is phospholipase A2, and the amino acid sequence of the phospholipase A2 is:

(a) the sequence of SEQ ID NO: 3; or (b) a sequence obtained after deleting four amino acids (from position 1 to position 4) from the sequence of SEQ ID NO: 3; or (c) an amino acid sequence obtained after mutating an amino acid into an alanine at position 69, 70, 73, 74, 77 or 90 of the sequence of SEQ ID NO: 3; or (d) a sequence which has 90% or more homology to the sequence of (a).

In one embodiment of the invention, the nucleotide sequence encoding the amino acid sequence of SEQ ID NO: 3 is shown in SEQ ID NO: 8.

In one embodiment of the invention, the amino acid sequence of the linker peptide is shown in SEQ ID NO: 1 (GGGGSGGGGS).

In one embodiment of the invention, the foreign protein is a prolyl endopeptidase.

In one embodiment of the invention, the amino acid sequence of the prolyl endopeptidase is shown in SEQ ID NO: 4.

In one embodiment of the invention, the fusion gene is obtained by ligating a gene fragment encoding the amino acid sequence of the phospholipase A2 with a gene fragment encoding a linker peptide (e.g. SEQ ID NO: 1), and ligating a gene fragment encoding prolyl endopeptidase (e.g. SEQ ID NO: 4) to the linker peptide fragment.

In one embodiment of the invention, the nucleotide sequence of the fusion gene is shown in SEQ ID NO: 2.

The second object of the invention is to provide a genetically engineered yeast expressing the fusion gene.

In one embodiment of the invention, the engineered yeast is an engineered *Pichia pastoris*, such as *Pichia pastoris* X33, GS115, KM71 or SMD1168, preferably *Pichia pastoris* GS115.

In one embodiment of the invention, a vector used for the expression may be pPIC9, pPIC3.5K, pPIC3.5, pPIC9K, PA0815 or pPICZα series and similar vectors thereof; preferably pPICZαA.

In one embodiment of the invention, the engineered *Pichia pastoris* is obtained by ligating the fusion gene with nucleotide sequence shown in SEQ ID NO.2 to pPICZαA first to obtain a recombinant vector pPICZαA-PLMH, then linearizing a recombinant plasmid and transforming the recombinant plasmid into a host *Pichia pastoris*.

In one embodiment of the invention, the host *Pichia pastoris* is *Pichia pastoris* GS115, or *Pichia pastoris* GS115 integrated with pPIC9K plasmids (in order to overcome the histidine defect of *Pichia pastoris* for ease of operation).

In one embodiment of the invention, a 6×His tag is added after the sequence of the fusion gene to facilitate isolation and purification.

The third object of the invention is to provide a method for producing a prolyl endopeptidase by using the fusion gene, an expression vector containing the fusion gene, or a genetically engineered yeast expressing the fusion gene.

In one embodiment of the invention, after being activated, the genetically engineered *Pichia pastoris* yeast expressing the fusion gene is inoculated into a BMGY medium, cultured at 30° C. and 200 r·min$^{-1}$ for 16-18 hr; when OD600 reaches 2-6, the culture medium is centrifuged, yeast cells are re-suspended in the BMMY medium and cultured at 28° C. and 250 r·min$^{-1}$, and 1% methanol is added every 24 h to induce expression.

In one embodiment of the invention, after being activated, the genetically engineered *Pichia pastoris* yeast expressing the fusion gene is inoculated into a fermentation tank for glycerol growth phase culture at 30° C., pH 5.5, in a BSM basal salt medium (containing 1.1 g·L$^{-1}$ of CaSO$_4$ (cp), 18.2 g·L$^{-1}$ of K$_2$SO$_4$(AR), 7.27 g·L$^{-1}$ of anhydrous magnesium sulfate (AR), 4.128 g·L$^{-1}$ of KOH (AR), 40 g·L$^{-1}$ of glycerol and 26.7 ml·L$^{-1}$ of 85% H$_3$PO$_4$). When glycerol in the BSM basal salt medium runs out and the dissolved oxygen value increases sharply, the glycerol transition phase starts and 50% (V/V) glycerol (containing 12 mL·L$^{-1}$ of PTM1, wherein PTM1 contains 6 g·L$^{-1}$ of copper sulfate pentahydrate, 0.089 g·L$^{-1}$ of potassium iodide, 3.0 g·L$^{-1}$ of magnesium sulfate monohydrate, 0.2 g·L$^{-1}$ of sodium molybdate, 0.02 g·L$^{-1}$ of boric acid, 42.2 g·L$^{-1}$ of zinc sulfate heptahydrate, 65 g·L$^{-1}$ of ferrous sulfate heptahydrate, 0.2 g·L$^{-1}$ of biotin, 0.5 g·L$^{-1}$ of cobalt chloride hexahydrate and 5 ml·L$^{-1}$ of sulfuric acid) is fed to the cells. When the cell OD600 value reaches 90-110, glycerol feeding is stopped and the induction phase starts after starving the cells for 0.5 hr, during which methanol is fed to the cells, the methanol concentration is maintained at 0.08-0.12%, and the culture temperature is controlled at 26-28° C.

The fourth object of the invention is to provide applications for prolyl endopeptidases produced by using the fusion gene, an expression vector containing the fusion gene, or a genetically engineered microorganism expressing the fusion gene.

The applications are in the fields like food, preparation medicine and molecular biology.

The applications include reducing the content of a sensitive protein in a beer fermentation broth, increasing the non-biological stability of beer, and removing the bitterness of a protein hydrolysate.

The applications also include preparing drugs for regulating glucose metabolism or pancreas functions.

The applications also include the use of the prolyl endopeptidase as an instrumental enzyme in molecular biology for being applied to protein sequence determination, peptide mapping analysis, digestion of specific loci, peptide chain modification and processing and the like.

The fifth object of the invention is to provide a method for improving the expression level of a foreign protein by means of phospholipase fusion expression. The method comprises sequentially ligating a gene fragment encoding a phospholipase A2, a linker peptide fragment encoding an amino acid sequence such as SEQ ID NO.1 (GGGGSGGGGS) and a gene fragment encoding a foreign protein to obtain a fusion gene, and then expressing the fusion gene.

In one embodiment of the invention, the fusion tag is phospholipase A2 having an amino acid sequence shown in SEQ ID NO: 3 or a sequence being 90% or more homologous to the sequence of SEQ ID NO: 3.

In one embodiment of the invention, the foreign protein is a prolyl endopeptidase having an amino acid sequence shown in SEQ ID NO: 4.

In one embodiment of the invention, the nucleotide sequence of the fusion gene is shown in SEQ ID NO: 2.

In the invention, the four proteins PLA$_2$, MBP, CBD and SUMO are used as a fusion tag to construct a fusion expression strain. Results show that compared with an original strain MOH, the extracellular protein expression level and enzyme activity of the four fusion proteins are increased to some extent, and, among them, the expression level of the target protein is the highest when PLA$_2$ is used as a fusion tag, which is 7.4 times higher than that of the original strain. Compared with other fusion tags, PLA$_2$ derived from *S. violaceoruber* A-2688 has the characteristics of being high in protein expression level (the highest extracellular protein concentration can reach 12 g·L$^{-1}$ in a 7 L fermentation tank for high-density fermentation) and low in molecular weight. The results of the study show that the secretory expression of a foreign protein can be effectively increased by using PLA$_2$ as a fusion tag.

EXAMPLES

Figure 1:
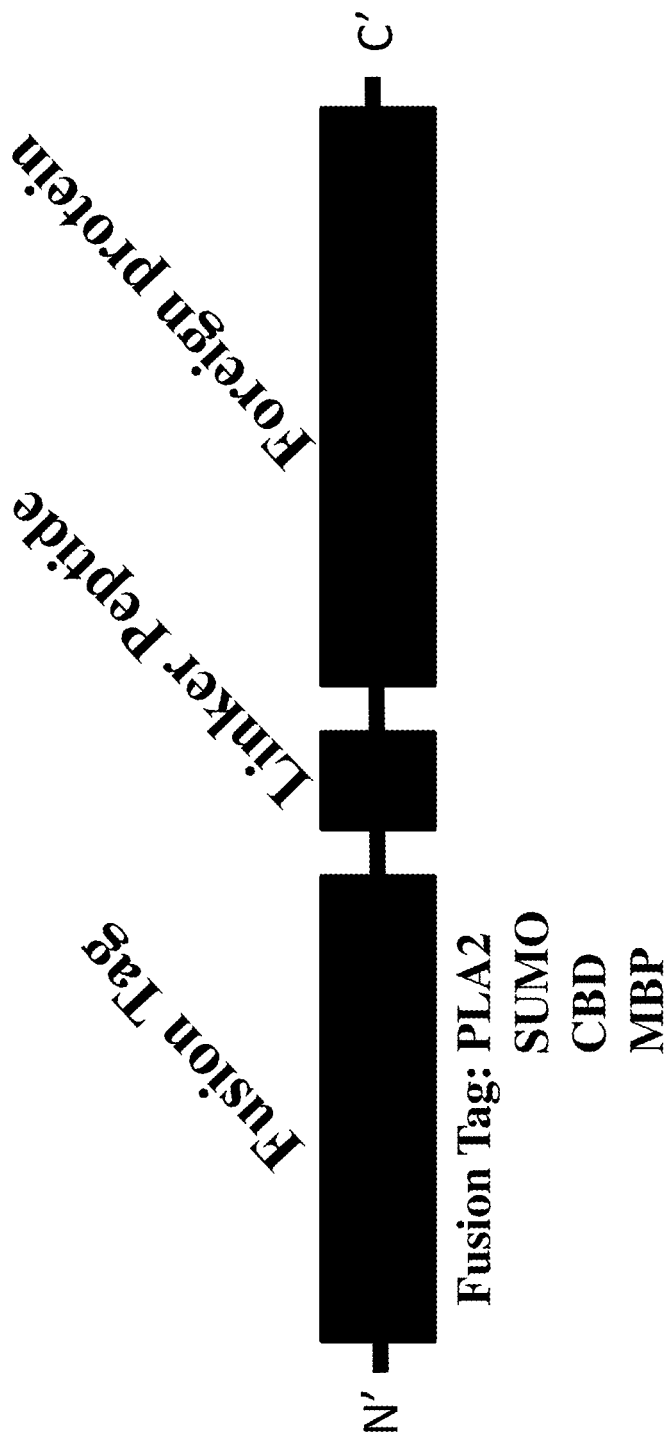
FIG. 1. Schematic diagram of the structure of the fusion gene of the invention.

Materials and Methods:

1. Method for Determining Protein Concentration

20 μl of supernatant of fermentation broth was added into wells of a 96-well plate, and then 200 μl of G250 staining reagent was added. Let it stand at room temperature for 3-5 minutes. The absorbance at 595 nm wavelength was measured with a spectrophotometer, and protein concentration in a sample was calculated according to a standard curve.

2. Method for Determining Protease Activity

A reaction system was consisted of 10 μl of enzyme solution, 10 μl of 5 mM substrate (Ala-Ala-Pro-pNA) and 80 μl of disodium hydrogen phosphate-citrate buffer. The reaction was carried out at 40° C. for 10 min, and the absorbance at 410 nm wavelength was measured with a spectrophotometer.

Definition of enzyme activity unit (U): under the enzyme activity determination conditions specified above, the amount of enzyme required to catalyze and decompose aforementioned substrate to generate 1 μmol of pNA per minute equals to a prolyl endopeptidase enzyme activity unit.

Enzyme activity calculation formula: enzyme activity $(U \cdot mL^{-1}) = \Delta A * V/(v1rbt)$, where, $\Delta A$: change in absorbance $(OD_{test} - OD_{blank})$; V: total volume of reaction system (mL); v1: sample amount (mL); r: molar extinction coefficient $(cm^2 \cdot \mu mol^{-1})$; b: optical path of a cuvette or a Elisa plate (cm); and t: reaction time (min).

3. Western Blot Analysis

Western blot analysis was conducted on supernatant and intracellular protein of a fusion protein shake flask fermentation, and the western blot procedure was as follows:

(1) Cut a protein gel to an appropriate size after conventional protein electrophoresis, and immerse the protein gels in a transfer buffer for being balanced.

(2) Cut a PVDF membrane and filter paper of the same size as the gel (8 pieces of filter paper for one PVDF membrane), and soak them in pure methanol first and then in the transfer buffer for 10 min.

(3) Neatly stack the PVDF membrane, the filter paper and the gel in a transfer box, wherein four layers of filter paper, the PVDF membrane, the gel and four layers of filter paper were arranged from bottom to top in sequence. Rolling gently with a roller to get rid of excess air bubbles and buffer every time a layer was applied; finally, absorbing surrounding buffer with a paper towel, closing a lid, and placing the transfer box in a transfer instrument.

(4) Transferring: turn on the power; select List, User Defined (this is an edited program 25 V, 1.0 A, 10 min) and Run in sequence.

(5) Take the PVDF membrane out after transferring, immerse the PVDF membrane in a blocking reagent, and gently shake in a decolorization shaker for 1 hr.

(6) Immerse the confined PVDF membrane in a primary antibody solution diluted in PBST (0.137 M NaCl, 0.0027 M KCl, 0.01 M $Na_2HPO_4$, 0.0018 M $KH_2PO_4$, 0.1% (v/v) Tween-20) with a dilution rate of 1:1000 (v/v), conduct shaking and incubation at room temperature for 1 hr. Wash the membrane with PBST 5 times, 10 min for each time.

(7) Immerse the PVDF membrane in a secondary antibody solution diluted with PBST at a ratio of 1:400 (v/v), and add an antibody pre-stained with a Marker at a ratio of 1:10000. Shake in the decolorization shaker for 1 hr. Wash the membrane again with PBST 5 times, 10 min for each time.

(8) Place the washed PVDF membrane in a chemiluminescent baseplate. Conduct elution with a chromogenic agent (A/B liquid mixed based on the ratio of 1:1), and take pictures with a gel imager.

Intracellular protein extraction was conducted with a one-step yeast active protein extraction kit purchased from Sangon Biotech (Shanghai) Co., Ltd.

4. Purification of Fusion Protein

A fermentation broth was centrifuged at 6000×g for 30 min after 84 hr of shake flask fermentation, pellets were discarded, a supernatant was collected, ultrafiltration concentration was conducted with a 30-kDa ultrafiltration tube, and the fermentation broth was precipitated with 60% ammonium sulfate $(NH_4)_2SO_4$ for 4 hr after concentration. Protein precipitation was dissolved in a 20 mM phosphate buffer (pH 5.0) and dialyzed overnight. The whole process was operated on ice at 4° C. A dialyzed protease solution was subjected to Ni column purification. Ni-NTA nickel column purification comprised the steps of: centrifuging 500 mL of fermented broth obtained by shake flask fermentation at 4° C. and 6300 rpm for 30 min, taking a supernatant, conducting filtration with a 0.22 μm aqueous phase microfiltration membrane, and then conducting concentration to 50 mL with a 30-kDa ultrafiltration tube. Protein purification was conducted with an AKTA purifier protein purification system by means of a conventional method. Before loading a sample, the system and a 5 mL Ni-NTA Superflow Cartridge chromatographic column were pre-equilibrated using a solution A, then the sample was loaded, and collection of flow through peaks needed to be noted. The system and the Ni chromatographic column were washed again with an equilibration solution for being equilibrated. Flushing was conducted with a 5% solution B prior to formally eluting with the solution B and collecting the protein, so as to elute off impurity proteins attached to the column. Linear elution was conducted with a 0-0.05 $mol \cdot L^{-1}$ eluant, collection of elution peaks needed to be noted, the flow rate was controlled to be 2 $mL \cdot min^{-1}$, and SDS-PAGE gel electrophoresis was conducted on the elution peaks for purity detection. SDS-PAGE analysis was conducted on the purified protein.

5. Mass Spectrum Identification of Fusion Protein PLMH

A recombinant protein sample was separated by conventional SDS-PAGE, stained and decolorized, then a target band to be identified was cut off, and enzyme protein verification was conducted through peptide mass fingerprinting. The method comprised the steps of:

(1) cutting off the target band on a gel with a scalpel blade and placing the target band in an EP tube (cutting a gel block into pieces in the size of about 1 mm³);

(2) adding 200-400 μL of 100 mM NH₄HCO₃/30% for decolorization, washing the gel, and removing the supernatant;

(3) adding 90 μL of 100 mM NH₄HCO₃ and 10 μL of 100 mM DTT into each tube, incubating at 56° C. for 30 min to reduce the protein;

(4) removing the supernatant, adding 100 μL of 100% CAN into each tube, and absorbing the 100% CAN after 5 min;

(5) adding 70 μL of 100 mM NH₄HCO₃ and 30 μL of 200 mM IAA into each tube, and keeping it dark for 20 min;

(6) removing the supernatant, adding 100 μL of 100 mM NH₄HCO₃ into each tube, and standing at room temperature for 15 min;

(7) removing the supernatant, adding 100 μL of 100% ACN, absorbing the 100% ACN after 5 min, and conducting lyophilization;

(8) after lyophilization, adding 5 μL of 2.5-10 ng·μL⁻¹ trypsin, and standing at 4° C. for 30-60 min for full imbibition of the gel blocks;

(9) adding about 20-30 μL of 25 mM NH₄HCO₃ buffer for reaction overnight at 37° C., lasting about 20 hr;

(10) sucking out an enzymatic hydrolysate and transferring to a new EP tube for lyophilization; and

(11) after completing sample preparation, adding 0.1% TFA for redissolving, conducting sample application, and conducting mass spectrum analysis.

6. Property Study of Fusion Protein PLMH (1) Method for determining optimum temperature: according to a method for determining enzyme activity, the reaction system was placed at 25-80° C. for reaction for 5 minutes.

(2) Method for determining temperature stability: a purified fusion protease solution was placed at 25-80° C. for 120 hr, and remaining enzyme activity was measured according to a conventional enzymatic activity determination method.

(3) Method for detecting optimum pH: buffers with different pH values were prepared, including 0.02 mol·L⁻¹ citrate phosphate buffer (pH 2.0-8.0), 0.05 mol·L⁻¹ Tris-HCl buffer (pH 9.0-10.5) and glycine/NaOH buffer (pH 11.0-12.0), and the enzyme activity of the prolyl endopeptidase in these pH ranges was measured with 100% relative enzyme activity as the highest enzyme activity.

(4) Method for detecting pH stability: the enzyme solution was placed in the above buffer for incubation at room temperature for 120 hr, and remaining enzyme activity was detected at pH 5.0 and 40° C.

(5) Using Ala-Ala-Pro-pNA as the substrate, a substrate solution with final substrate concentration of 0.1-1.0 mM was prepared, the activity of the prolyl endopeptidase was measured at 40° C., and corresponding kinetic parameters were calculated by means of double-reciprocal plot. All experiments have three repeats.

Example 1. Preparation of Fusion Genes (1) Gene source: a phospholipase A2 gene was derived from *Streptomyces violaceoruber* with the amino acid sequence of SEQ ID NO: 3, and the sequence was amplified from a pPIC9K-PLA2 plasmid previously constructed in our laboratory; a prolyl endopeptidase (PEP) gene MO was derived from *Aspergillus oryzae* with the amino acid sequence of SEQ ID NO: 4, and the sequence was amplified from a pPIC9K-MO plasmid previously constructed in the laboratory; and the amino acid sequences of a maltose binding protein (MBP), a cellulose binding domain (CBD) and a small ubiquitin-related modifier (SUMO) gene were shown in SEQ ID NO: 5, SEQ ID NO: 6 and SEQ ID NO: 7 respectively. The above genes were optimized according to *Pichia pastoris* codon preference and synthesized by Sangon Biotech (Shanghai) Co., Ltd.

(2) A fusion tag fragment comprising a phospholipase A2, an MBP, a CBD or a SUMO gene, and a PEP gene fragment were obtained through PCR amplification or chemical synthesis. After column purification, overlap extension PCR was conducted to obtain a fusion gene, wherein the fusion gene sequentially comprised a fusion tag fragment, a linker peptide and a PEP gene fragment, wherein the nucleotide sequence of the linker peptide (GGGGSGGGGS) was shown in SEQ ID NO: 1. The fusion genes comprising a phospholipase A2, an MEP, a CBD and a SUMO gene sequence are named as PLMH, MLMH, CLMH and SLMH, respectively. The nucleotide sequence of the fusion gene PLMH containing the fusion tag phospholipase A2 (nucleotide sequence shown in SEQ ID NO: 8) was shown in SEQ ID NO. 2. Primers used in the invention were shown in Table 1.

TABLE 1

Primers used in the invention

| Primers | Sequence (5'-3'') | Serial number |
|---|---|---|
| PLA2-F | ATCAGAATTCGCTCCACCTCAGGCTGC | SEQ ID NO: 9 |
| PLA2 R | ACAATCCTAAAGAACCACCACCACCAGAACCACCACCACCA AGAATTTTC | SEQ ID NO: 10 |
| CBD-F | AGAATTCCAGCAGACTGTCTGGGGACA | SEQ ID NO: 11 |
| CBD-R | AGAACCACCACCACCAATGCATTGGGCATA | SEQ ID NO: 12 |
| SUMO-F | AGAATTCGGTCACCATCATCATCATCA | SEQ ID NO: 13 |
| SUMO-R | AGAACCACCACCACCGGGATCAAACTCACC | SEQ ID NO: 14 |
| MBP-F | AGAATTCGCTAGTAAGATCGAAGAAGG | SEQ ID NO: 15 |
| MBP-R | AGAACCACCACCACCTCCAGCACCATCGCC | SEQ ID NO: 16 |

TABLE 1-continued

Primers used in the invention

| Primers | Sequence (5'-3'') | Serial number |
|---|---|---|
| PEP-F | GGTGGTGGTGGTTCTGGTGGTGGTGGTTCTTTAGGATTGT | SEQ ID NO: 17 |
| PEP-R | AGCGGCCGCCATAACTGCACCCTTAG | SEQ ID NO: 18 |

Among them, the underlined nucleotides were a restriction enzyme site, and the black bold nucleotides refer to the nucleotide sequence for the linker peptide.

Example 2. Construction of Recombinant Expression Vector

Example of the fusion gene PLMH:

The fusion gene fragment PLMH obtained from the Example 1 after column purification was subjected to A tail addition (aKaRa rTaq 0.5 μL, 10×PCR Buffer 5 μL, dNTP Mixture 4 μL and purified product 40.5 μL reacted for 15-20 min at 72° C.), then ligated to a pMD-19T vector, and then transformed into Escherichia coli. The plasmids of a transformant were extracted and sequenced, and the obtained validated recombinant plasmid was named pMD-19T-PLMH.

The plasmid pMD-19T-PLMH and pPICZαA were digested with EcoR I and Not I at the same time and then ligated to obtain a recombinant expression vector pPICZαA-PLMH containing the fusion gene PLMH (in the construction process of the recombinant plasmid, a 6×His tag was added to the C-terminal of the prolyl endopeptidase to facilitate isolation and purification).

In a similar manner, recombinant expression vectors pPICZαA-MLMH, pPICZαA-CLMH, pPICZαA-SLMH and pPICZαA-MOH were obtained. Among them, MOH was obtained by adding a 6×His tag to the C-terminal of an original prolyl endopeptidase during the construction of the recombinant plasmid.

Example 3. Construction of Genetically Engineered Bacteria

The recombinant expression vector pPICZαA-PLMH was used as an example to illustrate the process of constructing the genetically engineered bacteria.

The pPICZαA-PLMH was linearized with Sac I and then transformed into a P. Pichia GS115/pPIC9K yeast competent cell (pPIC9K was introduced into a host to overcome the histidine defect of the host for ease of culture).

Electrotransformation: transferring and mixing a tube of competent cells with the linearized plasmid, keeping it on ice for 3-5 min, and then transferring it into a 2 mm pre-cooled electrotransformation cup for electroporation. The parameters of an electroporation instrument were: voltage 1500 V, resistance 200Ω, and capacitance 25 μF. Immediately after electrotransformation, 1 mL of 1 mol·L$^{-1}$ sorbitol solution was added, evenly mixed and transferred to a 1.5 mL EP tube for resuscitation at 30° C. for 1 hr. The supernatant was removed after centrifugation with 100 μL remaining. A YPD+Zeocin plate was coated with the re-suspending bacterial cells, and single-colony transformants were obtained after culturing at 30° C. for 3 days in an incubator. Monoclonal strains were selected for validation. The validated strain was identified as GS115/pPIC9K/pPICZαA-PLMH P. Pichia strain that expresses the fusion gene PLMH, whose secreted proline protease was named PLMH.

In a similar manner, recombinant strains GS115/pPIC9K/pPICZαA-MLMH, GS115/pPIC9K/pPICZαA-CLMH and GS115/pPIC9K/pPICZαA-SLMH expressing fusion genes MLMH, CLMH, and SLMH and a recombinant strain GS115/pPIC9K/pPICZαA-MOH expressing the non-fusion/control gene MOH were prepared. Proline proteases secreted by the above strains were named MLMH, CLMH, SLMH and MOH proteins, respectively.

Example 4. Shake Flask Fermentation of Recombinant Strains Expressing Four Proline Proteases The recombinant strains were streaked and cultured on a YPD plate for about 3 days. Monoclonal strains were selected and placed in a 250 ml triangular flask containing 25 mL BMGY medium and cultured for 16-18 hr at 200 rpm, 30° C. The fermentation broth was centrifuged after OD600 reached 2-6, and yeast cells were re-suspended in 50 mL BMMY medium and cultured at 28° C., 250 rpm, and 1% methanol was added every 24 hr to induce exogenous protein expression. Sampling was conducted periodically to determine cell concentration, protein concentration and enzyme activity.

The results of shake flask fermentation of four recombinant strains expressing the fusion proteins and a control MOH strain were shown in FIG. 1. The results showed that the cell concentrations (OD600) of the five strains were almost identical during the 120-hour fermentation period (FIG. 1a). In terms of protein concentration, the extracellular protein concentrations of bacterial cells reached the peak at 96 hr (FIG. 1b), with the concentrations of PLMH, MLMH, CLMH, SLMH and MOH being 0.22±0.05 mg·ml$^{-1}$, 0.20±0.05 mg·ml$^{-1}$, 0.17±0.03 mg·ml$^{-1}$, 0.15±0.05 mg·ml$^{-1}$ and 0.12±0.04 mg·mF$^{-1}$, respectively, and the highest enzyme activities appeared at 84 hr (FIG. 1c), which were 280±7.1 U·L$^{-1}$, 187±6.9 U·L$^{-1}$ and 146±5.5 U·L$^{-1}$, 105±6.5 U·L$^{-1}$ and 38±7.2 U·L$^{-1}$, respectively. During shake flask fermentation, PLMH was higher than those of other three fusion proteins and the MOH protein in terms of total protein concentration and enzyme activity.

Example 5. Influences of Different Linker Peptides on Fusion Gene Expression A linker peptide GGGGSGGGGSKR (SEQ ID NO: 19) containing a KEX2 protease cleavage site and a linker peptide LEVLFQGPENLYFQS (SEQ ID NO: 20) containing two protease cleavage sites were used to replace the linker peptide GGGGSGGGGS in the previous fusion gene PLMH. Similar methods as described above were used to construct recombinant strains expressing the two fusion genes with different linker peptides and similar fermentation methods were used for culturing the same.

The expression level of the fusion gene with the GGGGSGGGGS as the linker peptide was shown in FIG. 1, and extracellular fermentation liquid enzyme activity reached 280 U·L$^{-1}$, whereas secretory expression of fusion enzymes using the other two linker peptides could not be achieved in Pichia pastoris, and enzyme activity was undetectable in a fermentation supernatant. These results showed that the selection of linker peptides can play a significant role in the expression of the fusion proteins.

Example 6. Western Blot Detection of Fusion Proteins

Figure 2:
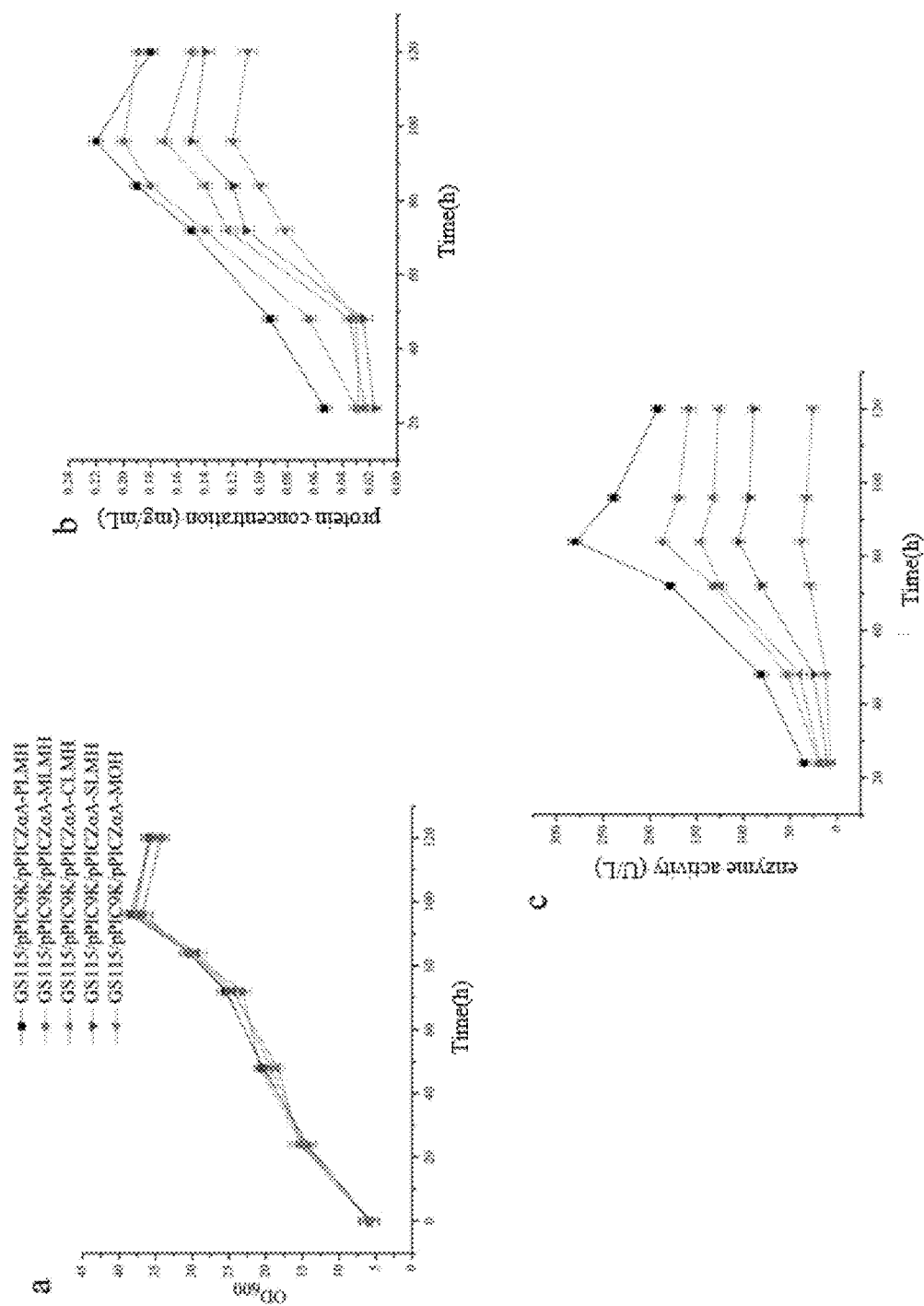
FIG. 2. Culture indicators of shake flask fermentation of genetically engineered *Pichia pastoris* GS115 strains, a: OD600; b: protein concentration; c: enzyme activity.

Western blot detection analysis was conducted on intracellular and extracellular proteins of the five recombinant strains. The results showed that a target band in the extracellular western blot (FIG. 2a) appeared in the vicinity of 80 kDa, and only one single band existed. At the same time, the results of western blot were consistent with extracellular protein content and enzyme activity, and proteins contents of the fusion proteins were higher than that of the MOH protein. The results of intracellular western blot (FIG. 2b) showed that the PEP protein synthesized by Pichia pastoris cells was completely secreted extracellularly, and there was no intracellular accumulation of the PEP protein.

Figure 3:
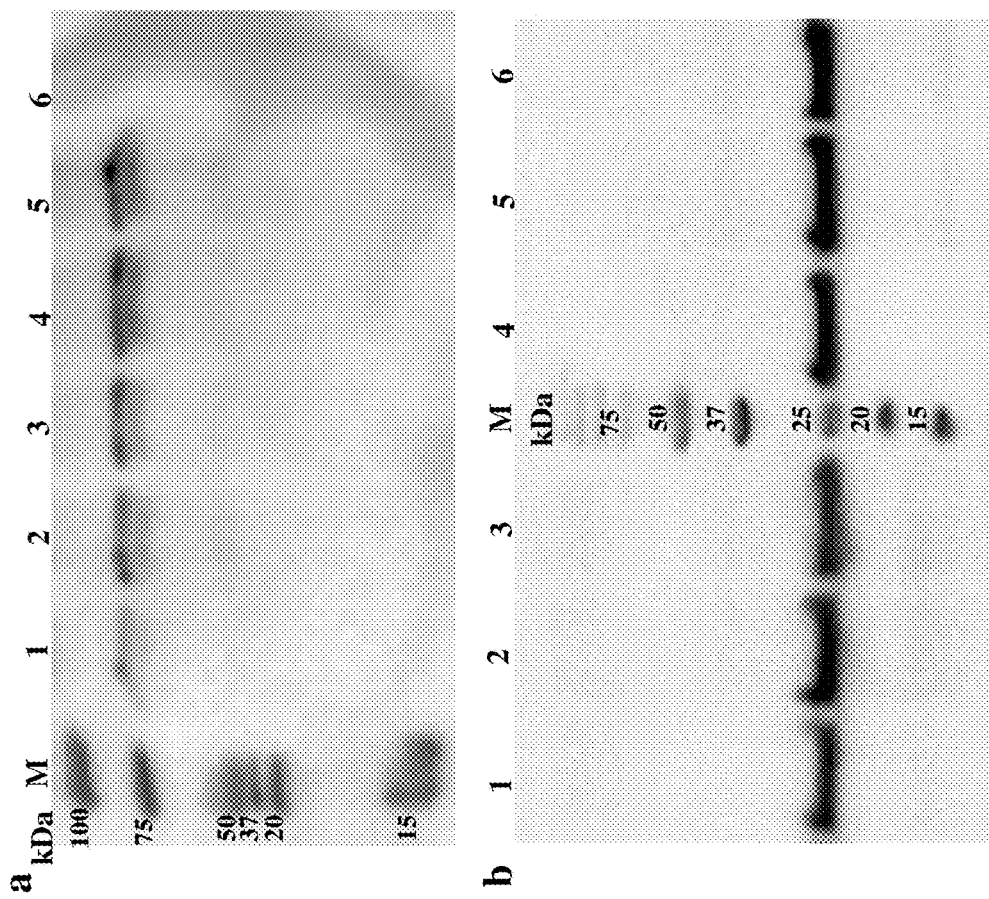
FIG. 3. Western blot results of proteins from genetically engineered *Pichia pastoris* GS115 strains. a: extracellular protein; b: intracellular protein; M: marker; 1-6 are proteins from MOH, SLMH, CLMH, MLMH, PLMH expressing cells and blank control, respectively.
Figure 4:
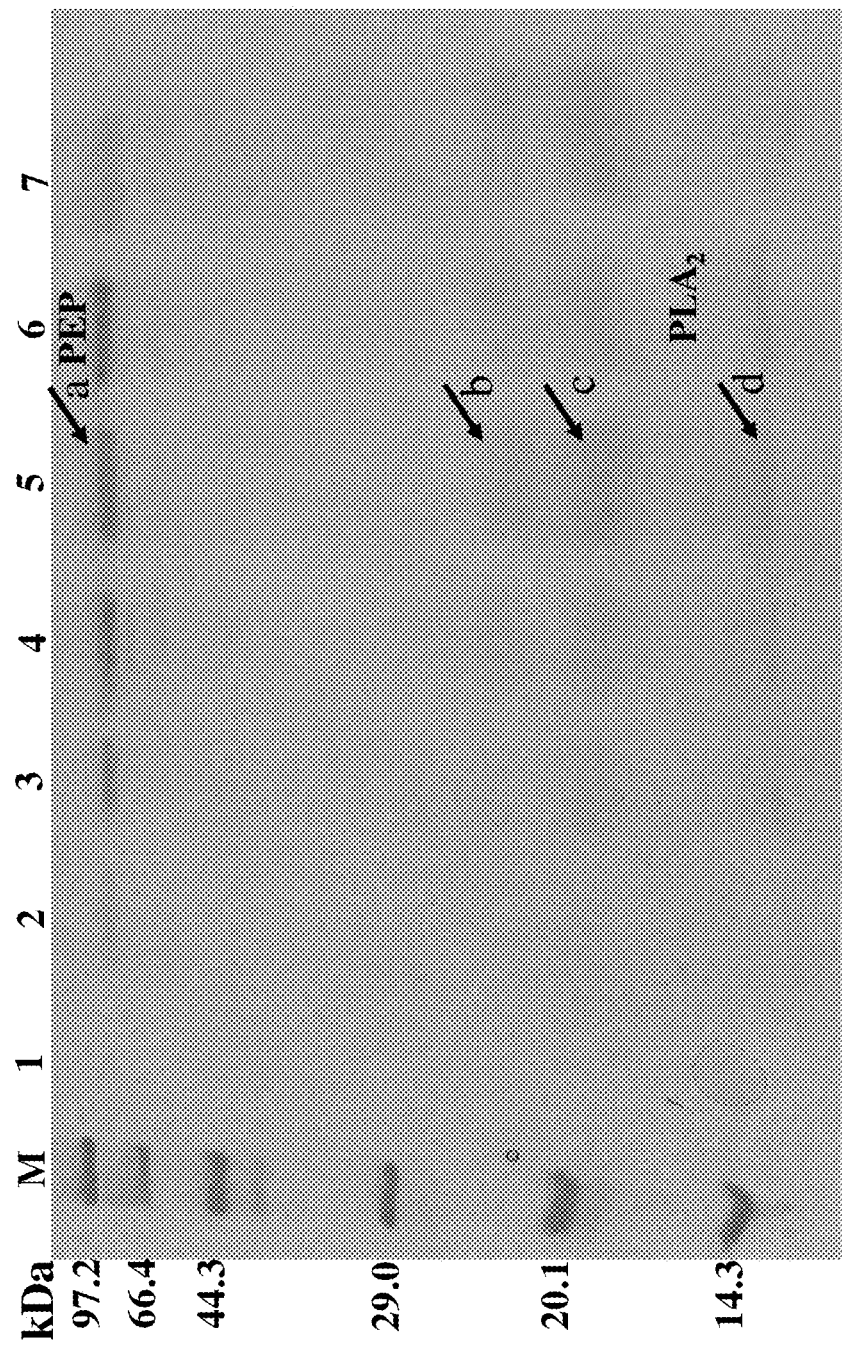
FIG. 4. SDS-PAGE Image of PLMH extracellular protein expression at different times of the shake flask fermentation. M: marker; 1-7 are shake flask fermentation broths after 0, 24, 48, 72, 84, 96 and 120 hr fermentation, respectively.

Example 7. SDS-PAGE Analysis and Mass Spectrum Identification of Fusion Protein PLMH The GS115/pPIC9K/pPICZαA-PLMH recombinant cells were cultured in a shake flask. The fermentation broth was collected at different times during the fermentation and analyzed using a SDS-PAGE. The SDS-PAGE analysis showed that the target bands in the vicinity of 80 kDa became brighter with the increase of fermentation time, and the target bands at 24, 18 and 14 kDa also became brighter. It indicated that with the increase of methanol induction time, the secretion of target proteins also increases. The four bands labeled as "a, b, c and d" in FIG. 3 were cut out from the SDS-PAGE gel and extracted for mass spectrum identification. The mass spectrum identification results showed that the protein at the position "a" in FIG. 3 was PEP, proteins at the positions "b, c, and d" are different forms of PLA2 protein, where the protein at the position "d" was the original PLA2 protein, and proteins at positions "b and c" were glycosylated PLA2 proteins (only the mass spectrum results of the protein band a and c were shown in FIG. 4.

Example 8. Purification of Fusion Protein PLMH and MOH Protein

PLMH and MOH proteins were purified using ultrafiltration, ammonium sulfate precipitation, dialysis, and Ni column purification. Yield and specific activity after each purification step were shown in Table 2. After ultrafiltration concentration, ammonium sulfate precipitation, dialysis, Ni column purification and other steps, PLMH and MOH proteins of electrophoretic purity were obtained.

TABLE 2

Purification of PLMH and MOH

| | Purification steps | Specific activity (U · mg$^{-1}$) | Purification factor | Yield (%) |
|---|---|---|---|---|
| PLMH | Fermentation supernatant | 2.9 | 1 | 100 |
| | Ultrafiltration (30 kDa) | 5.8 | 2 | 84 |
| | (NH$_4$)$_2$SO$_4$ precipitation (60%), dialysis | 10.2 | 3.5 | 17.5 |
| | Ni-NTA affinity purification | 43.2 | 14.9 | 8.9 |
| MOH | Fermentation supernatant | 3.2 | 1 | 100 |
| | Ultrafiltration (30 kDa) | 5.8 | 1.8 | 77 |
| | (NH$_4$)$_2$SO$_4$ precipitation (60%), dialysis | 10.2 | 3.2 | 16 |
| | Ni-NTA affinity purification | 49.3 | 15.4 | 4.6 |

Figure 5:
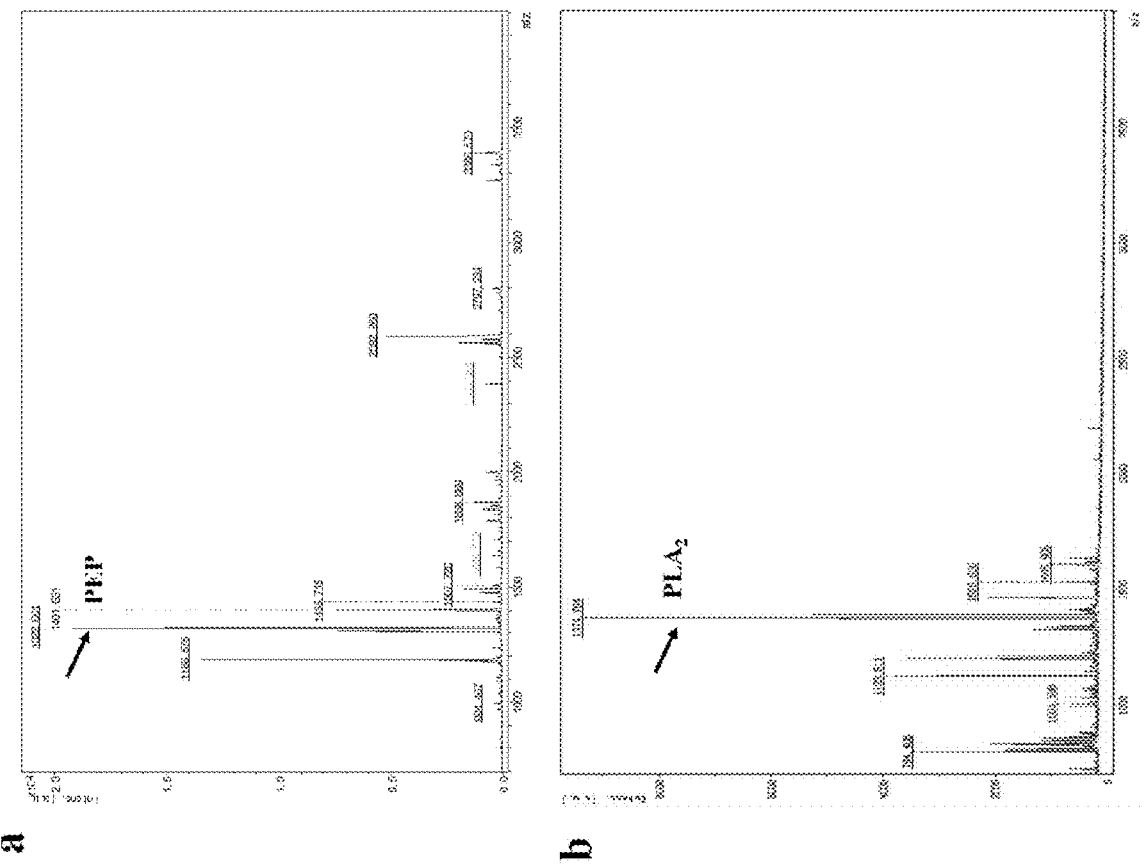
FIG. 5. Mass spectrum identification of fusion protein PEP and fusion tag PLA2.

Example 9. Comparison of Enzymatic Properties of Fusion Protein PLMH and MOH Protein Enzymatic property study was conducted on purified PLMH and MOH enzymes to determine the enzymatic properties such as optimum temperature, temperature stability, optimum pH, pH stability, km and kcat. As shown in FIG. 5, PLMH and MOH proteins had the same enzymatic properties. The optimum temperatures for both enzymes were 40° C. However, only 30% of enzyme activity was left after 120 min of incubation at 40° C., and when temperature reached 45° C., remaining enzyme activity was almost zero after 120 min of incubation. The optimum pH for both enzymes were 5.5, and the best stable phase was obtained at pH 6.0. After incubation at pH 5.0-7.5 for 120 min, remaining enzyme activity was still above 40%, indicating that PEP was relatively stable at a neutral pH.

In addition, Km, kcat and kcat/Km of the fusion protein PLMH were 0.23±0.01 mM, 112.51±0.02 S$^{-1}$ and 489.17 s$^{-1}$·mM$^{-1}$, respectively. Km, kcat and kcat/Km of MOH were 0.28±0.01 mM, 139.4±0.02 S$^{-1}$ and 496.4 s$^{-1}$·mM$^{-1}$, respectively. There was little difference between the two enzymes.

Example 10. Applications of Prolyl Endopeptidase PLMH (1) The Effect of Prolyl Endopeptidase/Proline Protease on the Reduction of Sensitive Proteins in Beer 500 ml fermented beer was filtered, added with a certain amount of PEP, and incubated in a water bath at 40° C. for 1 hr. It was then precipitated overnight with 100% saturated ammonium sulfate at 4° C., and centrifuged at 10,000 rpm for 30 min to collect the precipitate. The precipitate was dissolved by citrate buffer and the total protein of beer was obtained after dialysis at 4° C. Different concentrations of PLMH protein (5 U/L, 15 U/L, 25 U/L) was added to the beer total protein. After glycolysis for 3 hr at 40° C., SDS-PAGE electrophoresis was performed to detect the sensitive proteins.

Figure 6:
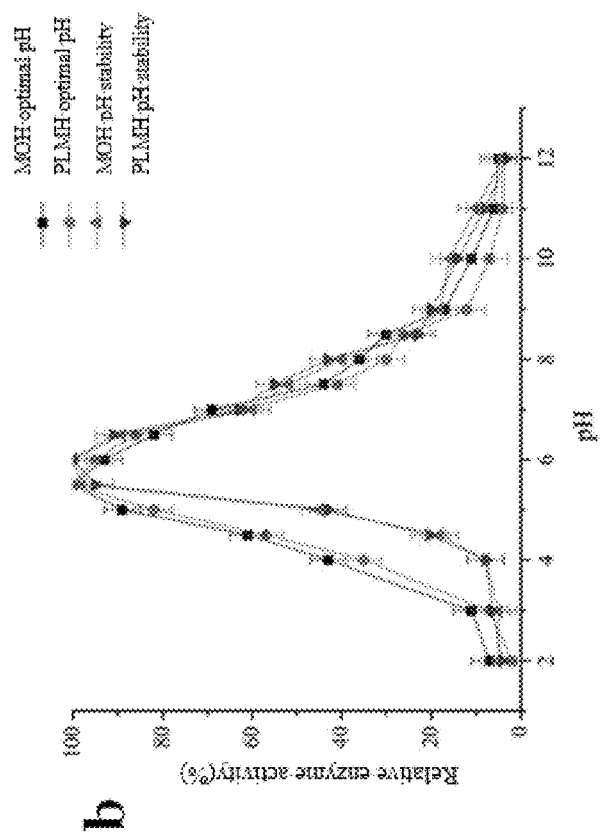
FIG. 6. Comparison of enzymatic properties of PLMH and MOH, a: optimum temperature and temperature stability; b: optimum pH and pH stability.
Figure 6:
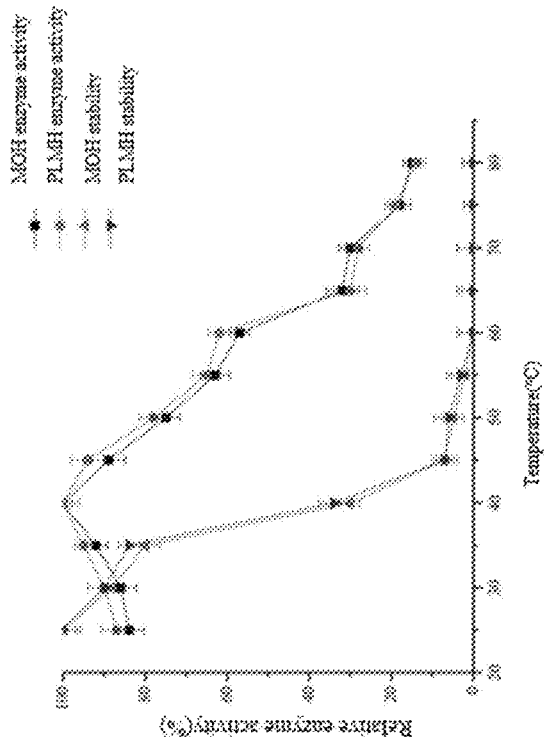
Figure 7:
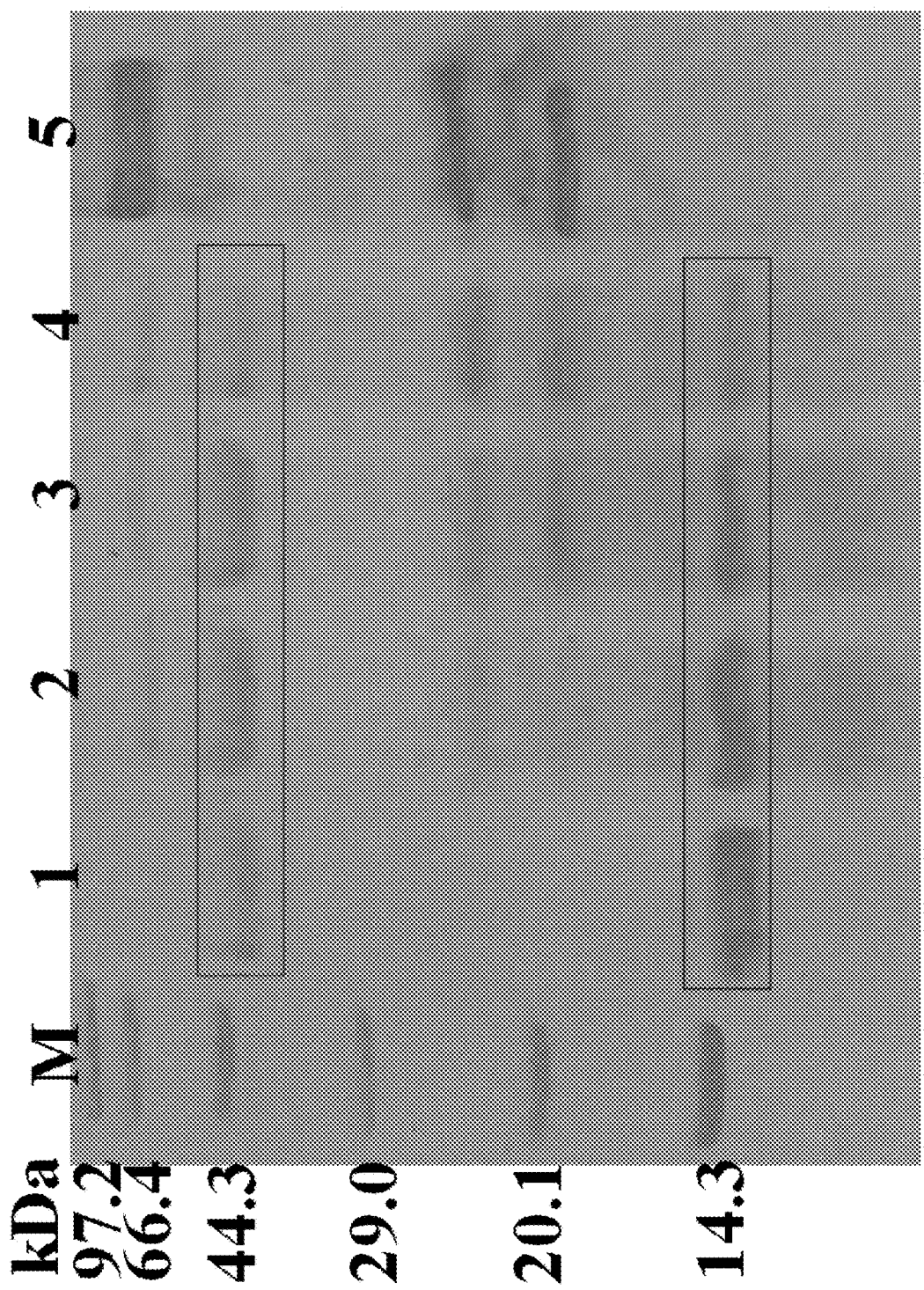
FIG. 7. Reduction of sensitive protein in beer fermentation broth by proline proteases; M: marker; 1-4: beer fermentation broth samples with addition of 0, 5, 15 and 25 $U \cdot L^{-1}$ proline protease; 5: proline protease protein.

From FIG. 6, it can be found that the sensitive proteins that cause turbidity of the beer fermentation broth are approximately 40 kDa and 12 kDa in size. Compared with the blank control, the proline protease can reduce the amount of sensitive proteins in the beer. With the increasing amount of proline protease added, the amount of large sensitive proteins in the beer was gradually decreased.

(2) Effects of Proline Proteases on Non-Biological Stability During Storage of Fermented Beer Prolyl endopeptidase PLMH of different concentrations (5 U·L$^{-1}$, 15 U·L$^{-1}$, and 25 U·L$^{-1}$) was added to filtered and sterilized beer fermentation broth and refrigerated at 4° C. Samples were collected every other week for turbidity determination. Three samples in each group were collected for 6 weeks.

The effect of the proline protease on the non-biological stability of the beer fermentation broth was determined. The accumulation of protein in beer during storage resulted in the increase of turbidity (EBC). The addition of the proline protease could reduce the turbidity during storage of beer, and this effect was increased with the increase of added proline protease. EBC was reduced to 0.3 after 15 U·L$^{-1}$ proline protease PLMH was added, indicating that the proline protease of the invention can be effectively applied to reduce the turbidity of beer.

Example 11. Production of Prolyl Endopeptidase Using the Genetically Engineered Strain A 7 L fermentation tank high-density fermentation was performed to produce prolyl endopeptidase PLMH using the genetically engineered strain GS115/pPIC9K/pPICZαA-PLMH containing the fusion gene PLMH. The enzyme activity of PLMH was measured after fermentation, and the highest enzyme activity reached 1800 U·L$^{-1}$.

The fermentation method was as follows:

The recombinant strain was cultured in the YPD medium for 16-18 hr, and the recombinant strain was inoculated into a 7 L fermentation tank for glycerol growth phase culture at 30° C. and pH 5.5, wherein the fermentation tank contained 2.1 L of BSM basal salt medium. When glycerol in the BSM basal salt medium was consumed and ran out and the dissolved oxygen value increased sharply, the glycerol transition phase started. 50% (V/V) glycerol (containing 12 mL·L$^{-1}$ of PTM1) was fed to the cells until the cell OD600 value reached 90-110, and glycerol feeding was then stopped. The induction phase started after starving the cells for 0.5 hr during which methanol was fed and maintained at the concentration of 0.08-0.12%, and temperature was controlled at 26-28° C.

The materials used in this example were as follows:

YPD medium: protein powder 20 g·L$^{-1}$, yeast powder 10 g·L$^{-1}$, glucose 20 g·L$^{-1}$;

BSM basal salt medium: CaSO$_4$(cp) 1.1 g·L$^{-1}$, K$_2$SO$_4$ (AR) 18.2 g·L$^{-1}$, anhydrous magnesium sulfate AR 7.27 g·L$^{-1}$, KOH(AR) 4.128 g·L$^{-1}$, glycerol 40 g·L$^{-1}$, 85% H3PO4 26.7 ml·L$^{-1}$;

PTM1: copper sulfate pentahydrate 6 g·L$^{-1}$, potassium iodide 0.089 g·L$^{-1}$, sulfate monohydrate 3.0 g·L$^{-1}$, sodium molybdate 0.2 g·L$^{-1}$, boric acid 0.02 g·L$^{-1}$, zinc sulfate heptahydrate 42.2 g·L$^{-1}$, ferrous sulfate septihydrate 65 g·L$^{-1}$, biotin 0.2 g·L$^{-1}$, cobalt chloride hexahydrate 0.5 g·L$^{-1}$, sulfuric acid 5 ml·L$^{-1}$.

Example 12. Effects of Different PLA2 Mutants on the Production of the Fusion Proteins Having PEP and PLA2 Mutants Since phospholipase A2 has phospholipase activity, the phospholipase activity of the enzyme can have a negative effect on the fermentation and the expression of the fusion gene containing phospholipase A2. While the fusion of phospholipase A2 to a foreign protein (e.g. PEP) facilitates the secretion of the fusion protein, the phospholipase activity of the enzyme is neither needed nor desirable for the expression and activity of the foreign/target protein. Therefore, two groups of phospholipase A2 mutations were designed to study the effects of mutations on the phospholipase A2 activity and the expression level of the fusion protein.

The first group of mutation was a truncation mutation, that is, four amino acids (from position 1 to position 4) were deleted from the amino acid sequence of phospholipase A2. The results showed that phospholipase activity could still be detected from the recombinant strain expressing the fusion gene with the PLA2 truncation mutation. The expression of the fusion protein was not affected, and the proline protease activity of the fusion protein with the truncated PLA2 mutant did not change compared to that of the fusion protein with the PLA2.

The second group of mutation was point mutations in which an amino acid at position 69, 70, 73, 74, 77 or 90 of the sequence of phospholipase A2 (SEQ ID NO: 3) was mutated into an alanine. The results showed that phospholipase activity could not be detected in a fermentation supernatant from the recombinant strain expressing the fusion gene containing one of the six PLA2 point mutations. But the activity of proline protease was not affected, and the proline protease activity of the fusion protein with a mutated phospholipase did not change compared to that of the fusion protein with the wild-type PLA2.

Based on the above findings, it was suggested that the fusion protein with a proline protease fused to one of the six point mutant PLA2 can achieve the best results.

What is claimed is:

1. A fusion gene, comprising a gene fragment encoding a fusion tag, a gene fragment encoding a linker peptide, and a gene fragment encoding a foreign protein, wherein the linker peptide has the amino acid sequence of SEQ ID NO:1, wherein the fusion tag is selected from a group of a phospholipase A2 and mutants thereof consisting of
   (a) a phospholipase A2 having the amino acid sequence of SEQ ID NO: 3;
   (b) a mutant of the sequence (a), wherein said mutant of the sequence (a) has the first four amino acids deleted from the sequence (a);
   (c) a mutant of the sequence (a), wherein said mutant of the sequence (a) has the amino acid at position 69, 70, 73, 74, 77 or 90 mutated to alanine in the sequence (a); and
   (d) a phospholipase A2 mutant having 90% or more homology to the sequence (a).

2. The fusion gene of claim 1, wherein the foreign protein is a prolyl endopeptidase.

3. The fusion gene of claim 2, wherein the prolyl endopeptidase has the amino acid sequence of SEQ ID NO: 4.

4. The fusion gene of claim 1, wherein the fusion gene is inserted into an expression vector.

5. The fusion gene of claim 4, wherein the expression vector with the fusion gene is transformed in a host microorganism to obtain an genetically engineered microorganism expressing the fusion gene.

6. The fusion gene of claim 5, wherein the genetically engineered microorganism is yeast *Pichia pastoris* comprising the fusion gene of claim 1 inserted into vector pPICZαA.

7. A method for expressing a foreign protein, comprising constructing a fusion gene of claim 1 and expressing the fusion gene.

8. The method of claim 7, wherein the foreign protein is a prolyl endopeptidase.

9. The method of claim 8, wherein the fusion tag comprises a phospholipase A2 having the amino acid sequence of SEQ ID NO: 3.

10. The method of claim 8, wherein the fusion tag comprises a mutant of SEQ ID NO:3, wherein said mutant of SEQ ID NO:3 has a point mutation to alanine at position 69, 70, 73, 74, 77 or 90.

* * * * *

SEQUENCE LISTING

<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Synthetic amino acid sequence

<400> SEQUENCE: 1

Gly Gly Gly Gly Ser Gly Gly Gly Gly Ser
1               5                   10

<210> SEQ ID NO 2
<211> LENGTH: 2085

<212> TYPE: DNA
<213> ORGANISM: Artificial Sequence
<220> FEATURE:
<223> OTHER INFORMATION: Synthetic DNA

<400> SEQUENCE: 2

```
gctccacctc aggctgctcc agctgataaa cctcaagttt tagcttcctt tacccaaact      60
tccgctagtt ctcagaatgc atggctggcc gcaaatcgta accaatctgc atgggccgct     120
tacgaatttg attggtcaac tgacttgtgt tcccaagctc cagataaccc attcggcttt     180
ccctttaaca cagcttgtgc taggcatgat ttcggttaca gaattacaa ggcagccggt      240
tctttcgatg caaacaagtc acgaatcgac agtgccttct atgaagacat gaagagagtc     300
tgcactgggt ataccggaga gaaaaacact gcctgtaatt ctacagcctg gacgtattac     360
caggccgtga aaattcttgg tggtggtggt tctggtggtg gtggttcttt aggattgttt     420
agaggctcta gatacatgag agaacttcaa ctggcagcag agcttaacct agatcctaga     480
agtcttttcta agaaaaacac agtccacagt gttctggcca agctaacac tcagattgaa      540
aaagtgacca cagaatacat cacaatcccc atcgatcaca cgatacctc agttggaact      600
tatcagaaca gattttgggt taacgacgac tattacgaag ccggaagacc tatcatcatg     660
tacgatgcag gagaaaccaa tgctgaatct attgccaaga accatctaac ttcatcccta     720
tcctttttca gaaaaatatt ggaagacaca catgccatgg gtatcatttg gaacataga      780
tactatggaa atagtacccc tttccccatt tctagagaca ctcctcccga acattttaag     840
tatctgacta ccaaacaggc cctggaagat attccctatt tcgctagaaa tttctcaaga     900
cctaaatttg ctgagcatga cttgacccca tcttcaaccc cttgggtctt ggttggtgga     960
tcatatgctg gtattagagc tgcatttgcc agaaataaat atccagacgt cattttttgct   1020
gcatactctt catctgcccc agtacaagct cagttgaata tgtccatata ctatgatcaa    1080
gtctatagag gcttggtggg tcatggtttt gaaaactgcg ccaaggatat acacgctgct    1140
ctgggttaca ttgatcagca gttaagtaac aatcacacag cagccgctat taagaaattg    1200
ttctttggcc caggcgctga tcagaatagt aacgaaggtt ttactgctgc tctagctacc    1260
atttactcct actttcaaaa ttacggattg gatggtccag aaggaacttt gagagaatta    1320
tgtgaacatt tagaagtcga tccaactaca aaggaggctg ctggaccaga tggatttgca    1380
cctgtaagag gatcaaagca tgttgccgag agatgggcag catggccagc ttttacccca    1440
ttggttaaca acttcatgga gactaattgc agaggcttat ctgatcctgc taagccatct    1500
tgtaagcttg atatgacata ctacgacccc gactctatta gttggagttg gcagtattgt    1560
actgagtggg gtttctatca atcctccaat ttcggtcccc actcccttct ttccagatac    1620
caaaccctgg agtatcaaca agaggtttgt aataatcaat ttgctttggc agttgctaac    1680
ggtgtgttgc cttcataccc acaaactgaa gcactgaata aggagtatgg tggttggaac    1740
ataagaccta gtaatacatt cttcaccggt ggagagttcg atccatggag aacattgtcc    1800
atgcttacta ccgaggacat cgccccagag gtagcccctg acggtatcac tttctcaact    1860
aagattccta actgcggcga gacttccgag gataaagttt tggttacttt attgaaagat    1920
tccgagcact gttacgactt tcaaggttta tctactgaag gaaaggctgc cagagacctg    1980
ttcaaggaag ctctaacaaa atggttgcct tgttttcaagc catcatcttc taaagcttct   2040
atggtgaacg ttacacaagc cgaaattact aagggtgcag ttatg                    2085
```

<210> SEQ ID NO 3

```
<211> LENGTH: 126
<212> TYPE: PRT
<213> ORGANISM: Artificial Sequence
<220> FEATURE:
<223> OTHER INFORMATION: Protein translated from Synthetic DNA

<400> SEQUENCE: 3

Ala Pro Pro Gln Ala Pro Ala Asp Lys Pro Gln Val Leu Ala Ser
1               5                   10                  15

Phe Thr Gln Thr Ser Ala Ser Gln Asn Ala Trp Leu Ala Ala Asn
                20                  25                  30

Arg Asn Gln Ser Ala Trp Ala Ala Tyr Glu Phe Asp Trp Ser Thr Asp
            35                  40                  45

Leu Cys Ser Gln Ala Pro Asp Asn Pro Phe Gly Phe Pro Phe Asn Thr
    50                  55                  60

Ala Cys Ala Arg His Asp Phe Gly Tyr Arg Asn Tyr Lys Ala Ala Gly
65                  70                  75                  80

Ser Phe Asp Ala Asn Lys Ser Arg Ile Asp Ser Ala Phe Tyr Glu Asp
                85                  90                  95

Met Lys Arg Val Cys Thr Gly Tyr Thr Gly Glu Lys Asn Thr Ala Cys
            100                 105                 110

Asn Ser Thr Ala Trp Thr Tyr Gln Ala Val Lys Ile Leu
            115                 120                 125

<210> SEQ ID NO 4
<211> LENGTH: 559
<212> TYPE: PRT
<213> ORGANISM: Artificial Sequence
<220> FEATURE:
<223> OTHER INFORMATION: Protein translated from Synthetic DNA

<400> SEQUENCE: 4

Leu Gly Leu Phe Arg Gly Ser Arg Tyr Met Arg Glu Leu Gln Leu Ala
1               5                   10                  15

Ala Glu Leu Asn Leu Asp Pro Arg Ser Leu Ser Lys Lys Asn Thr Val
                20                  25                  30

His Ser Val Leu Ala Lys Ala Asn Thr Gln Ile Glu Lys Val Thr Thr
            35                  40                  45

Glu Tyr Ile Thr Ile Pro Ile Asp His Asn Asp Thr Ser Val Gly Thr
    50                  55                  60

Tyr Gln Asn Arg Phe Trp Val Asn Asp Tyr Tyr Glu Ala Gly Arg
65                  70                  75                  80

Pro Ile Ile Met Tyr Asp Ala Gly Glu Thr Asn Ala Glu Ser Ile Ala
                85                  90                  95

Lys Asn His Leu Thr Ser Ser Leu Ser Phe Phe Arg Lys Ile Leu Glu
            100                 105                 110

Asp Thr His Ala Met Gly Ile Ile Trp Glu His Arg Tyr Tyr Gly Asn
        115                 120                 125

Ser Thr Pro Phe Pro Ile Ser Arg Asp Thr Pro Glu His Phe Lys
    130                 135                 140

Tyr Leu Thr Thr Lys Gln Ala Leu Glu Asp Ile Pro Tyr Phe Ala Arg
145                 150                 155                 160

Asn Phe Ser Arg Pro Lys Phe Ala Glu His Asp Leu Thr Pro Ser Ser
                165                 170                 175

Thr Pro Trp Val Leu Val Gly Gly Ser Tyr Ala Gly Ile Arg Ala Ala
            180                 185                 190

Phe Ala Arg Asn Lys Tyr Pro Asp Val Ile Phe Ala Ala Tyr Ser Ser
```

```
            195                 200                 205
Ser Ala Pro Val Gln Ala Gln Leu Asn Met Ser Ile Tyr Tyr Asp Gln
210                 215                 220

Val Tyr Arg Gly Leu Val Gly His Gly Phe Glu Asn Cys Ala Lys Asp
225                 230                 235                 240

Ile His Ala Ala Leu Gly Tyr Ile Asp Gln Gln Leu Ser Asn Asn His
                245                 250                 255

Thr Ala Ala Ile Lys Lys Leu Phe Phe Gly Pro Gly Ala Asp Gln
            260                 265                 270

Asn Ser Asn Glu Gly Phe Thr Ala Ala Leu Ala Thr Ile Tyr Ser Tyr
                275                 280                 285

Phe Gln Asn Tyr Gly Leu Asp Gly Pro Glu Gly Thr Leu Arg Glu Leu
            290                 295                 300

Cys Glu His Leu Glu Val Asp Pro Thr Thr Lys Glu Ala Ala Gly Pro
305                 310                 315                 320

Asp Gly Phe Ala Pro Val Arg Gly Ser Lys His Val Ala Glu Arg Trp
                325                 330                 335

Ala Ala Trp Pro Ala Phe Thr Pro Leu Val Asn Asn Phe Met Glu Thr
            340                 345                 350

Asn Cys Arg Gly Leu Ser Asp Pro Ala Lys Pro Ser Cys Lys Leu Asp
                355                 360                 365

Met Thr Tyr Tyr Asp Pro Asp Ser Ile Ser Trp Ser Trp Gln Tyr Cys
370                 375                 380

Thr Glu Trp Gly Phe Tyr Gln Ser Ser Asn Phe Gly Pro His Ser Leu
385                 390                 395                 400

Leu Ser Arg Tyr Gln Thr Leu Glu Tyr Gln Gln Val Cys Asn Asn
                405                 410                 415

Gln Phe Ala Leu Ala Val Ala Asn Gly Val Leu Pro Ser Tyr Pro Gln
            420                 425                 430

Thr Glu Ala Leu Asn Lys Glu Tyr Gly Gly Trp Asn Ile Arg Pro Ser
            435                 440                 445

Asn Thr Phe Phe Thr Gly Gly Glu Phe Asp Pro Trp Arg Thr Leu Ser
450                 455                 460

Met Leu Thr Thr Glu Asp Ile Ala Pro Glu Val Ala Pro Asp Gly Ile
465                 470                 475                 480

Thr Phe Ser Thr Lys Ile Pro Asn Cys Gly Glu Thr Ser Glu Asp Lys
                485                 490                 495

Val Phe Gly Tyr Leu Leu Lys Asp Ser Glu His Cys Tyr Asp Phe Gln
                500                 505                 510

Gly Leu Ser Thr Glu Gly Lys Ala Ala Arg Asp Leu Phe Lys Glu Ala
            515                 520                 525

Leu Thr Lys Trp Leu Pro Cys Phe Lys Pro Ser Ser Ser Lys Ala Ser
            530                 535                 540

Met Val Asn Val Thr Gln Ala Glu Ile Thr Lys Gly Ala Val Met
545                 550                 555

<210> SEQ ID NO 5
<211> LENGTH: 376
<212> TYPE: PRT
<213> ORGANISM: Artificial Sequence
<220> FEATURE:
<223> OTHER INFORMATION: Protein translated from Synthetic DNA

<400> SEQUENCE: 5

Ala Ser Lys Ile Glu Glu Gly Lys Leu Val Ile Trp Ile Asn Gly Asp
```

```
              1               5                      10                    15
            Lys Gly Tyr Asn Gly Leu Ala Glu Val Gly Lys Lys Phe Glu Lys Asp
                          20                      25                    30
            Thr Gly Ile Lys Val Thr Val Glu His Pro Asp Lys Leu Glu Glu Lys
                          35                      40                    45
            Phe Pro Gln Val Ala Ala Thr Gly Asp Gly Pro Asp Ile Ile Phe Trp
                          50                      55                    60
            Ala His Asp Arg Phe Gly Gly Tyr Ala Gln Ser Gly Leu Leu Ala Glu
            65                          70                      75                    80
            Ile Thr Pro Asp Lys Ala Phe Gln Asp Lys Leu Tyr Pro Phe Thr Trp
                                  85                      90                    95
            Asp Ala Val Arg Tyr Asn Gly Lys Leu Ile Ala Tyr Pro Ile Ala Val
                                  100                     105                   110
            Glu Ala Leu Ser Leu Ile Tyr Asn Lys Asp Leu Leu Pro Asn Pro Pro
                          115                     120                   125
            Lys Thr Trp Glu Glu Ile Pro Ala Leu Asp Lys Glu Leu Lys Ala Lys
                          130                     135                   140
            Gly Lys Ser Ala Leu Met Phe Asn Leu Gln Glu Pro Tyr Phe Thr Trp
            145                         150                     155                   160
            Pro Leu Ile Ala Ala Asp Gly Gly Tyr Ala Phe Lys Tyr Glu Asn Gly
                                  165                     170                   175
            Lys Tyr Asp Ile Lys Asp Val Gly Val Asp Asn Ala Gly Ala Lys Ala
                                  180                     185                   190
            Gly Leu Thr Phe Leu Val Asp Leu Ile Lys Asn Lys His Met Asn Ala
                          195                     200                   205
            Asp Thr Asp Tyr Ser Ile Ala Glu Ala Ala Phe Asn Lys Gly Glu Thr
                          210                     215                   220
            Ala Met Thr Ile Asn Gly Pro Trp Ala Trp Ser Asn Ile Asp Thr Ser
            225                         230                     235                   240
            Lys Val Asn Tyr Gly Val Thr Val Leu Pro Thr Phe Lys Gly Gln Pro
                                  245                     250                   255
            Ser Lys Pro Phe Val Gly Val Leu Ser Ala Gly Ile Asn Ala Ala Ser
                                  260                     265                   270
            Pro Asn Lys Glu Leu Ala Lys Glu Phe Leu Glu Asn Tyr Leu Leu Thr
                          275                     280                   285
            Asp Glu Gly Leu Glu Ala Val Asn Lys Asp Lys Pro Leu Gly Ala Val
                          290                     295                   300
            Ala Leu Lys Ser Tyr Glu Glu Glu Leu Ala Lys Asp Pro Arg Ile Ala
            305                         310                     315                   320
            Ala Thr Met Glu Asn Ala Gln Lys Gly Glu Ile Met Pro Asn Ile Pro
                                  325                     330                   335
            Gln Met Ser Ala Phe Trp Tyr Ala Val Arg Thr Ala Val Ile Asn Ala
                                  340                     345                   350
            Ala Ser Gly Arg Gln Thr Val Asp Glu Ala Leu Lys Asp Ala Gln Thr
                          355                     360                   365
            Leu Ile Asn Gly Asp Gly Ala Gly
                          370                     375
```

<210> SEQ ID NO 6
<211> LENGTH: 36
<212> TYPE: PRT
<213> ORGANISM: Artificial Sequence
<220> FEATURE:
<223> OTHER INFORMATION: Protein translated from Synthetic DNA

<400> SEQUENCE: 6

Gln Gln Thr Val Trp Gly Gln Cys Gly Gln Gly Trp Ser Gly Pro
1               5                   10                  15

Thr Ser Cys Val Ala Gly Ser Ala Cys Ser Thr Leu Asn Pro Tyr Tyr
            20                  25                  30

Ala Gln Cys Ile
        35

<210> SEQ ID NO 7
<211> LENGTH: 105
<212> TYPE: PRT
<213> ORGANISM: Artificial Sequence
<220> FEATURE:
<223> OTHER INFORMATION: Protein translated from Synthetic DNA

<400> SEQUENCE: 7

Gly His His His His His Gly Ser Leu Gln Glu Glu Lys Pro Lys
1               5                   10                  15

Glu Gly Val Lys Thr Glu Asn Asp His Ile Asn Leu Lys Val Ala Gly
            20                  25                  30

Gln Asp Gly Ser Val Val Gln Phe Lys Ile Lys Arg His Thr Pro Leu
        35                  40                  45

Ser Lys Leu Met Lys Ala Tyr Cys Glu Arg Gln Gly Leu Ser Met Arg
    50                  55                  60

Gln Ile Arg Phe Arg Phe Asp Gly Gln Pro Ile Asn Glu Thr Asp Thr
65                  70                  75                  80

Pro Ala Gln Leu Glu Met Glu Asp Glu Asp Thr Ile Asp Val Phe Gln
                85                  90                  95

Gln Gln Thr Gly Gly Glu Phe Asp Pro
            100                 105

<210> SEQ ID NO 8
<211> LENGTH: 378
<212> TYPE: DNA
<213> ORGANISM: Artificial Sequence
<220> FEATURE:
<223> OTHER INFORMATION: Synthetic DNA

<400> SEQUENCE: 8
gctccacctc aggctgctcc agctgataaa cctcaagttt tagcttcctt tacccaaact      60
tccgctagtt ctcagaatgc atggctggcc gcaaatcgta accaatctgc atgggccgct     120
tacgaatttg attggtcaac tgacttgtgt tcccaagctc cagataaccc attcggcttt     180
ccctttaaca cagcttgtgc taggcatgat ttcggttaca gaattacaa ggcagccggt      240 tctttcgatg caaacaagtc acgaatcgac agtgccttct atgaagacat gaagagagtc     300
tgcactgggt ataccggaga gaaaaacact gcctgtaatt ctacagcctg gacgtattac     360
caggccgtga aaattctt                                                   378

<210> SEQ ID NO 9
<211> LENGTH: 27
<212> TYPE: DNA
<213> ORGANISM: Artificial Sequence
<220> FEATURE:
<223> OTHER INFORMATION: Synthetic DNA

<400> SEQUENCE: 9
atcagaattc gctccacctc aggctgc                                          27

<210> SEQ ID NO 10
<211> LENGTH: 50
<212> TYPE: DNA
<213> ORGANISM: Artificial Sequence
<220> FEATURE:
<223> OTHER INFORMATION: Synthetic DNA

<400> SEQUENCE: 10
acaatcctaa agaaccacca ccaccagaac caccaccacc aagaattttc                50

<210> SEQ ID NO 11
<211> LENGTH: 27
<212> TYPE: DNA
<213> ORGANISM: Artificial Sequence
<220> FEATURE:
<223> OTHER INFORMATION: Synthetic DNA

<400> SEQUENCE: 11
agaattccag cagactgtct ggggaca                                         27

<210> SEQ ID NO 12
<211> LENGTH: 30
<212> TYPE: DNA
<213> ORGANISM: Artificial Sequence
<220> FEATURE:
<223> OTHER INFORMATION: Synthetic DNA

<400> SEQUENCE: 12
agaaccacca ccaccaatgc attgggcata                                      30

<210> SEQ ID NO 13
<211> LENGTH: 27
<212> TYPE: DNA
<213> ORGANISM: Artificial Sequence
<220> FEATURE:
<223> OTHER INFORMATION: Synthetic DNA

<400> SEQUENCE: 13
agaattcggt caccatcatc atcatca                                         27

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14
agaaccacca ccaccgggat caaactcacc                                      30

<210> SEQ ID NO 15
<211> LENGTH: 27
<212> TYPE: DNA
<213> ORGANISM: Artificial Sequence
<220> FEATURE:
<223> OTHER INFORMATION: Synthetic DNA

<400> SEQUENCE: 15
agaattcgct agtaagatcg aagaagg                                         27

<210> SEQ ID NO 16
<211> LENGTH: 30
<212> TYPE: DNA
<213> ORGANISM: Artificial Sequence
<220> FEATURE:
<223> OTHER INFORMATION: Synthetic DNA

```
<400> SEQUENCE: 16
agaaccacca ccacctccag caccatcgcc                                         30

<210> SEQ ID NO 17
<211> LENGTH: 40
<212> TYPE: DNA
<213> ORGANISM: Artificial Sequence
<220> FEATURE:
<223> OTHER INFORMATION: Synthetic DNA

<400> SEQUENCE: 17
ggtggtggtg gttctggtgg tggtggttct ttaggattgt                              40

<210> SEQ ID NO 18
<211> LENGTH: 26
<212> TYPE: DNA
<213> ORGANISM: Artificial Sequence
<220> FEATURE:
<223> OTHER INFORMATION: Synthetic DNA

<400> SEQUENCE: 18
agcggccgcc ataactgcac ccttag                                             26

<210> SEQ ID NO 19
<211> LENGTH: 12
<212> TYPE: PRT
<213> ORGANISM: Artificial Sequence
<220> FEATURE:
<223> OTHER INFORMATION: Protein translated from Synthetic DNA

<400> SEQUENCE: 19

Gly Gly Gly Gly Ser Gly Gly Gly Gly Ser Lys Arg
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Protein translated from Synthetic DNA

<400> SEQUENCE: 20

Leu Glu Val Leu Phe Gln Gly Pro Glu Asn Leu Tyr Phe Gln Ser
1               5                   10                  15
```